(12) United States Patent
Shoji

(10) Patent No.: US 6,954,065 B2
(45) Date of Patent: Oct. 11, 2005

(54) EDDY-CURRENT PROBE

(75) Inventor: Shigeru Shoji, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 10/938,541

(22) Filed: Sep. 13, 2004

(65) Prior Publication Data

US 2005/0062470 A1 Mar. 24, 2005

(30) Foreign Application Priority Data

Sep. 18, 2003 (JP) .................................. 2003-326174

(51) Int. Cl.⁷ .......................... G01R 33/12; G01B 7/00; G01N 27/72
(52) U.S. Cl. ...................................... 324/240; 324/228
(58) Field of Search .......................... 324/209, 219–220, 324/228–232, 234–244, 252, 260–261

(56) References Cited

U.S. PATENT DOCUMENTS 6,784,662 B2 * 8/2004 Schlicker et al. ........... 324/242
2001/0054894 A1 * 12/2001 Goldfine et al. ........ 324/207.17

FOREIGN PATENT DOCUMENTS

| JP | 07-083884 | 3/1995 |
| JP | 09-189682 | 7/1997 |
| JP | 11-248685 | 9/1999 |
| JP | 2002-090490 | 3/2002 |

OTHER PUBLICATIONS

Miyagoshi et al., "Feasibility of Inspecting Defects in Printed Circuit Boards by Using Eddy–Current Testing Techniques", Journal of the Magnetics Society of Japan, vol. 23, No. 4–2, pp 1613–1616, 1999 (cited in specification).
Yamada et al., "Trend of Detection Techniques Using Planar–Type Micro–Eddy–Current Testing", Journal of the Magnetics Society of Japan, vol. 23, No. 7, pp. 1817–1825, 1999 (cited in specification).

* cited by examiner

*Primary Examiner*—Bot LeDynh
(74) *Attorney, Agent, or Firm*—Burns, Doane, Swecker & Mathis

(57) ABSTRACT

An eddy-current probe according to the present invention comprises: a substrate having a first surface facing to a subject to be tested and a second surface opposite to said first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. The substrate has a non-planar form having at least one convex-surface portion on the first surface, and the at least one eddy-current sensor is formed on at least one concave-surface portion formed on the second surface, which is corresponding to the at least one convex-surface portion.

12 Claims, 11 Drawing Sheets

EDDY-CURRENT PROBE

PRIORITY CLAIM

This application claims priority from Japanese patent application No. 2003-326174, filed on Sep. 18, 2003, which is incorporated herein by reference.

BACKGROUND OF THE INVENTION

1. Field of the Invention

The present invention relates to an eddy-current probe that is able to detect object's shapes, defects and so on nondestructively.

2. Description of the Related Art

Eddy-current testing (ECT) technique is frequently utilized for nondestructive testing of distorted surfaces of important metal machine parts used in a nuclear power plant, an airplane and so on, such as turbine blades, various pipes and airplane wings. Generally, such an ECT probe using the eddy-current includes mainly an exciting coil and a detector coil for detecting a magnetic field based on an eddy-current induced by an alternating magnetic field generated by the excited coil. Such a technique is described in for example, Japanese Patent Publications Nos. 07-083884A, 09-189682A, 11-248685A and 2002-090490A.

Further, a planar-type ECT probe for inspecting printed circuit boards is proposed, including a meander-type exciting coil and a pick-up coil for the eddy-current detection which are formed on a flexible planar substrate. Such a probe is described in for example, T. Miyagoshi, D. Kacprzak, S. Yamada and M. Iwahara, "Feasibility of Inspecting Defects in Printed Circuit Boards by Using Eddy-Current Testing Techniques", Journal of the Magnetics Society of Japan, Vol. 23, No. 4–2, pp. 1613–1616, 1999, and S. Yamada and M. Iwahara, "Trend of Detection Techniques Using Planar-Type Micro-Eddy-Current Testing Probes", Journal of the Magnetics Society of Japan, Vol. 23, No. 7, pp. 1817–1825, 1999.

Recently, in such an ECT probe, an element for detecting the eddy-current, that is, an eddy-current sensor has been intended to be miniaturized, and to be improved in resolution and sensitivity. In order to improve its detecting resolution, as well as to miniaturize it, the ECT probe has been required to have less spacing between the sensor and a subject.

It is difficult for the planar-type ECT probe using a planar substrate to constantly keep the spacing between the surfaces of the substrate and of a subject much small. In some cases, the surfaces of the substrate and of the subject are almost in contact with each other. Further, when the subject has distorted surfaces, the ECT probe using a flexible thin substrate is desirable to be utilized to follow the surfaces smoothly. However, it is impossible to follow such a flexible substrate in no contact with the subject's surface.

When the surfaces of the substrate used in the planar-type ECT probe and of the subject are almost in contact with each other, an adsorption phenomenon (sticktion) is likely to occur between the surfaces of the substrate and of the subject.

When the sticktion occurs, some external-force application is needed to remove the probe substrate from the subject's surface against the sticktion. The application is likely to damage the probe substrate. The weaker is the strength of the substrate, the damage by the sticktion occurs more frequently. Because the flexible substrate has a small thickness and a weak mechanical strength, the durability and lifetime of the planar-type ECT probe depend largely on the occurrence of the sticktion, especially in the measurement of the distorted surface where the substrate inevitably has a contact with the subject's surface.

This problem tends greatly to appear in micro-defect detection on the smooth surface of the substrate.

BRIEF SUMMARY OF THE INVENTION

It is therefore an object of the present invention to provide an eddy-current probe for high resolution testing, possessing very high performances of the durability and lifetime by reducing an occurrence probability of the sticktion.

An eddy-current probe according to the present invention comprises: a substrate having a first surface facing to a subject to be tested and a second surface opposite to the first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. Especially, according to the present invention, the substrate has a non-planar form having at least one convex-surface portion on the first surface, and the at least one eddy-current sensor is formed on at least one concave-surface portion formed on the second surface, which is corresponding to the at least one convex-surface portion.

Because the first surface of the substrate facing to the subject (the measurement surface) has a non-planar form having the at least one convex-surface portion and therefore has a small facing/contact area with the subject's surface, the sticktion hardly occurs. Even if the sticktion occurs, much less external-force application should be needed to remove the probe from the subject's surface against the sticktion. Consequently, a damage probability by the sticktion is drastically reduced, and therefore, the durability and lifetime can be improved in a large extent. Further, because the at least one eddy-current sensor is formed on the at least one concave-surface portion formed on the second surface (the opposite surface to the measurement surface), which is corresponding to the at least one convex-surface portion, the distance between the subject's surface and the eddy-current sensor does not increase, and therefore, a high performance of resolution is provided.

Preferably, the at least one convex-surface portion has a waved convex form where the substrate is curved along a traverse direction (X direction). In the case, it is preferable that the at least one convex-surface portion is a single convex-surface portion or a plurality of convex-surface portions.

It is also preferable that the substrate is a flexible substrate.

Further, an eddy-current probe according to the present invention comprises: a substrate having a first surface facing to a subject to be tested and a second surface opposite to the first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. Especially, according to the present invention, the first surface of the substrate has a plurality of concaves and convexes.

Because the first surface of the substrate (the measurement surface) has a plurality of concaves and convexes, the sticktion hardly occurs. Even if the sticktion occurs, much less external-force application should be needed to remove the probe from the subject's surface against the sticktion. Consequently, a damage probability by the sticktion is drastically reduced. Therefore, the durability and lifetime of the eddy-current probe show no decrease, even when a high resolution is obtained by putting the measurement surface of the probe toward the subject's surface as closely as possible to minimize the distance between the subject's surface and the eddy-current sensor.

Preferably, the surface having a plurality of concaves and convexes is a rough surface by such as a blast finishing or an embossed surface.

Preferably, a lubricant layer, a diamond-like carbon (DLC) layer, or both of a DLC layer and a lubricant layer are formed on the first surface having a plurality of concaves and convexes. The lubricant layer, the DLC layer, or both of the DLC layer and the lubricant layer formed on the surface can prevent the sticktion more surely, and reduce the wear-outs of the measurement surface of the substrate and of the subject's surface.

Furthermore, an eddy-current probe according to the present invention comprises: a substrate having a first surface facing to a subject to be tested and a second surface opposite to the first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. Especially, according to the present invention, the first surface of the substrate has a plurality of grooves.

Because the first surface of the substrate (the measurement surface) has a plurality of grooves, the sticktion hardly occurs. Even if the sticktion occurs, much less external-force application should be needed to remove the probe from the subject's surface against the sticktion. Consequently, a damage probability by the sticktion is drastically reduced. Therefore, the durability and lifetime of the eddy-current probe show no decrease, even when a high resolution is obtained by putting the measurement surface of the probe toward the subject's surface as closely as possible to minimize the distance between the subject's surface and the eddy-current sensor.

Preferably, a plurality of grooves are grooves extended along a traverse direction (X direction) of the substrate, grooves extended along a longitudinal direction (Z direction) of the substrate, or grooves extended along an oblique direction to the traverse direction (X direction) of the substrate.

Preferably, a lubricant layer, a DLC layer, or both of a DLC layer and a lubricant layer are formed on the first surface having a plurality of grooves. The lubricant layer, the DLC layer, or both of the DLC layer and the lubricant layer formed on the surface can prevent the sticktion more surely, and reduce the wear-outs of the measurement surface of the substrate and of the subject's surface.

Further, an eddy-current probe according to the present invention comprises: a substrate having a first surface facing to a subject to be tested and a second surface opposite to the first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. Especially, according to the present invention, the first surface of the substrate has a plurality of holes.

Because the first surface of the substrate (the measurement surface) has a plurality of holes, the sticktion hardly occurs. Even if the sticktion occurs, much less external-force application should be needed to remove the probe from the subject's surface against the sticktion. Consequently, a damage probability by the sticktion is drastically reduced. Therefore, the durability and lifetime of the eddy-current probe show no decrease, even when a high resolution is obtained by putting the measurement surface of the probe toward the subject's surface as closely as possible to minimize the distance between the subject's surface and the eddy-current sensor.

Preferably, the holes are blind holes or through holes.

Preferably, a lubricant layer, a DLC layer, or both of a DLC layer and a lubricant layer are formed on the first surface having a plurality of holes. The lubricant layer, the DLC layer, or both of the DLC layer and the lubricant layer formed on the surface can prevent the sticktion more surely, and reduce the wear-outs of the measurement surface of the substrate and of the subject's surface.

Furthermore, an eddy-current probe according to the present invention comprises: a substrate having a first surface facing to a subject to be tested and a second surface opposite to the first surface; an exciting coil formed on the second surface, having a pair of current lines in parallel with each other through which exciting currents flow in opposite directions to each other during testing, for generating an alternate magnetic field applied to the subject by the exciting currents; and at least one eddy-current sensor positioned on a central axis between the pair of current lines on the second surface of the substrate, for detecting a magnetic field generated newly from the subject by an eddy-current induced by the alternate magnetic field. Especially, according to the present invention, the substrate includes a lubricant layer, a DLC layer, or both of the DLC layer and the lubricant layer formed on the first surface.

The lubricant layer, the DLC layer, or both of the DLC layer and the lubricant layer formed on the first surface of the substrate (measurement surface) can reduce the sticktion, and the wear-outs of the measurement surface of the substrate and of the subject's surface.

Preferably, the at least one eddy-current sensor is a single eddy-current sensor or a plurality of eddy-current sensors aligned on the central axis between said pair of current lines.

It is also preferable that the at least one eddy-current sensor is a magnetoresistive element. In the case, the magnetoresistive element is preferably a giant magnetoresistive element or a tunnel magnetoresistive element.

It is also preferable that the at least one eddy-current sensor is a detection coil.

Preferably, the exciting coil is a meander-type coil.

It is also preferable that the exciting coil comprises a coil conductor layer formed on the substrate and an insulating layer covering the coil conductor layer.

DETAILED DESCRIPTION OF THE INVENTION

Figure 1:
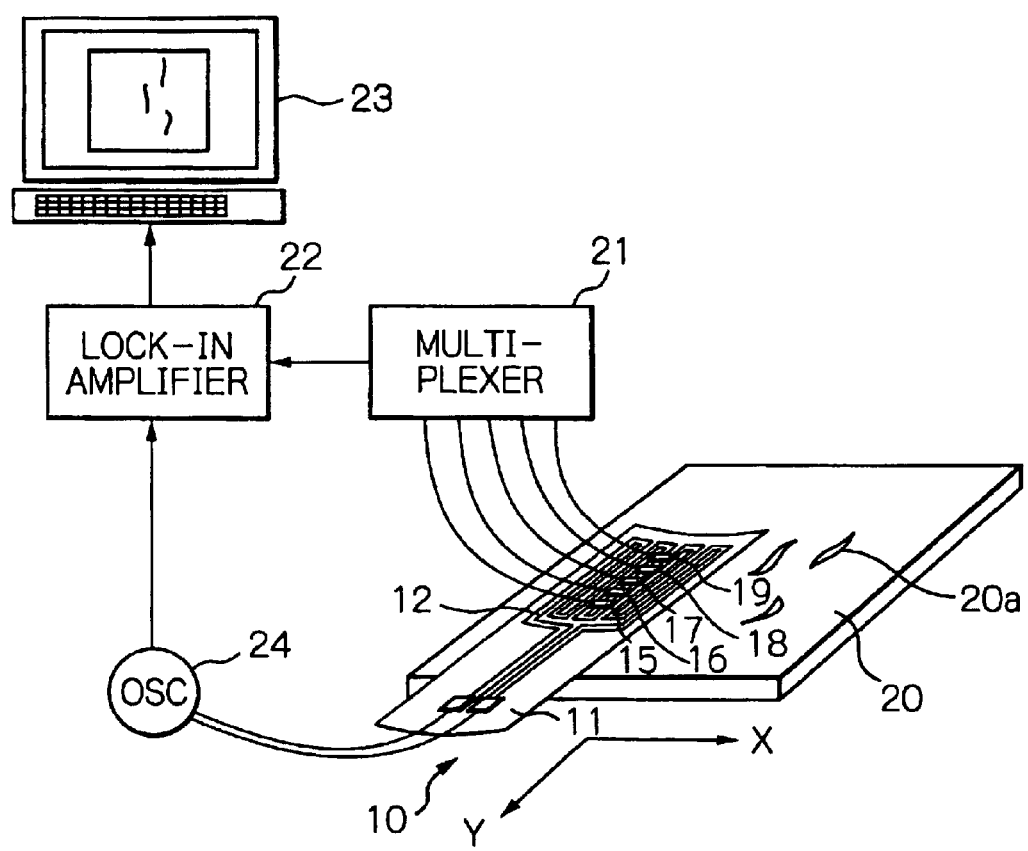
FIG. 1 shows a diagram schematically illustrating a configuration of an testing system using the eddy-current according to a preferred embodiment of the present invention.
Figure 2:
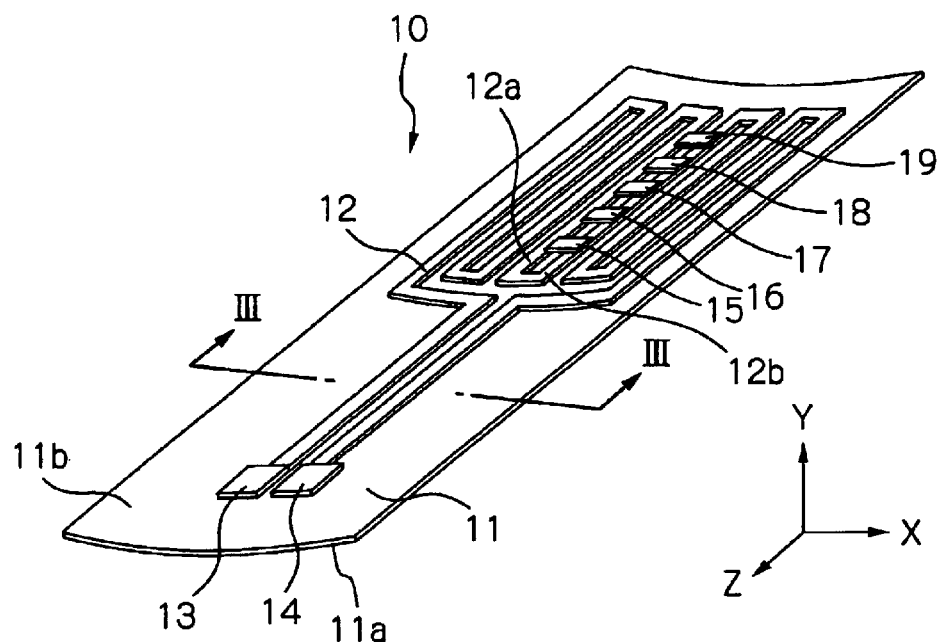
FIG. 2 shows a perspective view schematically illustrating a configuration of the ECT probe according to the embodiment in FIG. 1.
Figure 3:
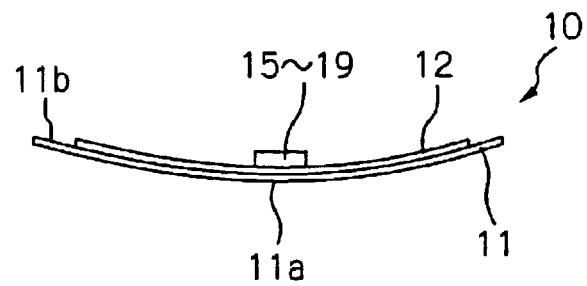
FIG. 3 shows a cross-sectional view taken along with line III—III in FIG. 2.

FIG. 1 shows a diagram schematically illustrating a configuration of an testing system using the eddy-current according to a preferred embodiment of the present invention, FIG. 2 shows a perspective view schematically illustrating a configuration of the ECT probe according to the embodiment in FIG. 1, and FIG. 3 shows a cross-sectional view taken along with line III—III in FIG. 2.

In these figures, reference numeral 10 indicates an ECT probe, 11 indicates its flexible substrate formed of an insulative material such as polyimide, 12 indicates a meander-type exciting coil including coil conductors formed as a planar pattern turned back on the opposite surface 11$b$ to the measurement surface 11$a$ of the substrate 11, 13 and 14 indicate a pair of electrode terminals formed on the substrate 11, which is connected electrically to both ends of the exciting coil 12, 15 to 19 indicate thin-film chips bonded on the exciting coil 12, each of which is mounted with a GMR element (eddy-current sensor) such as an SVMR element, 20 indicates a subject, 20$a$ indicates a defect such as a flaw and a crack appearing on the subject 20, 21 indicates a multiplexer connected electrically to the each GMR element in the ECT probe 10, which applies these GMR elements with a sense current and takes out signals from the each GMR element, 22 indicates a lock-in amplifier that receives the signals from the each GMR element through the multiplexer 21 and detects the signal's level, 23 indicates a computer that processes the input signals from the lock-in amplifier, displays the results and so on, and 24 indicates a power supply for alternate magnetic field, which provide the exciting coil 12 in the ECT probe 10 with an alternate exciting current and provide the lock-in amplifier 22 with the exciting current as reference signals, respectively.

The exciting coil 12 includes a coil conductor layer formed on the insulative substrate 11 and an insulating layer covering the coil conductor layer. An exciting part of the exciting coil 12 has a plurality of current lines that extend in parallel with each other to Z direction on the substrate 11, and are turned back at both ends. During testing, alternate exciting currents with opposite directions to each other flow through the current lines adjacent to each other, respectively.

The thin-film chips 15 to 19 are aligned on a central axis of a pair of current lines 12a and 12b positioned at the center in the X direction on the exciting coil 12. These thin-film chips 15 to 19 are bonded on the opposite surface to the subject 20 in the exciting coil 12.

Each of the thin-film chips 15 to 19 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, as understood from FIG. 3, the substrate 11 has a non-planar form curved along a traverse direction (X direction) where the measurement surface 11a shows a waveform of a single convex-surface. The thin-film chips 15 to 19 are mounted, via the exciting coil 12, on the opposite surface 11b of the substrate 11, which is a single concave-surface corresponding to the single convex-surface.

Because the measurement surface 11a on the substrate showing a waveform of a single convex-surface has a small facing/contact area with the subject 20, the sticktion hardly occurs. Even if the sticktion occurs, much less external-force application should be needed to remove the probe from the subject 20 against the sticktion. Consequently, a damage probability by the sticktion is drastically reduced, and therefore, the durability and lifetime can be improved in a large extent. Further, because the thin-film chips 15 to 19 are mounted on the concave-surface of the opposite surface 11b of the substrate 11, the distance between the surface of the subject 20 and the GMR element does not increase, and therefore, a high performance of resolution is provided.

Figure 4:
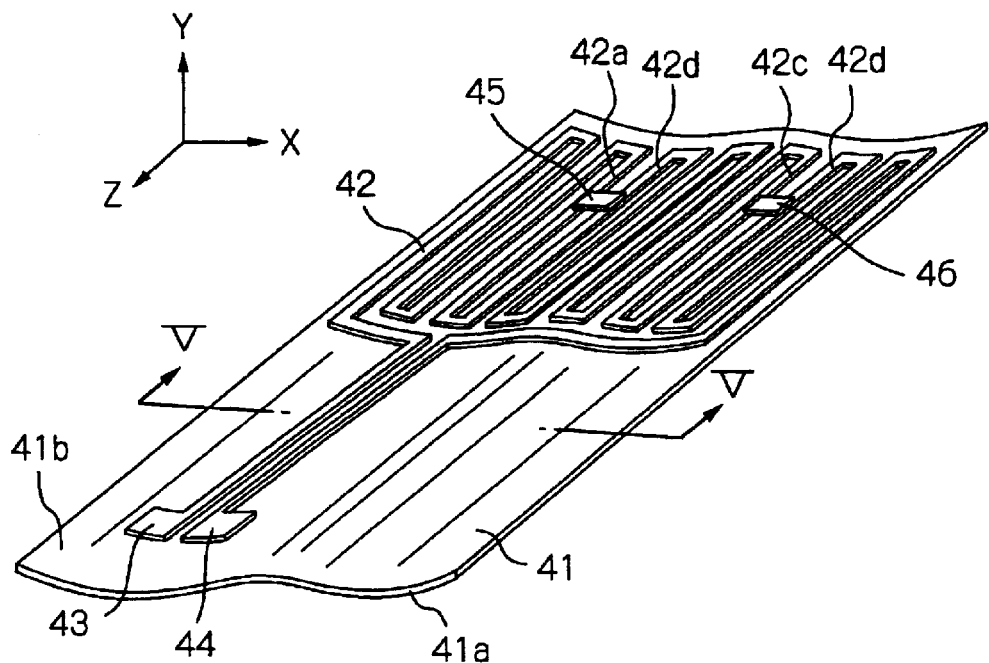
FIG. 4 shows a perspective view schematically illustrating a configuration of the ECT probe according to another embodiment of the present invention.
Figure 5:
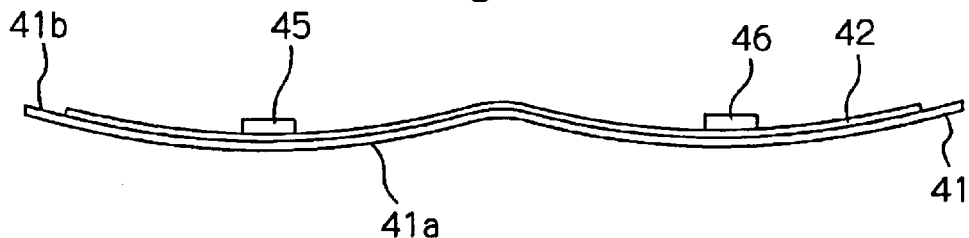
FIG. 5 shows a cross-sectional view taken along with line V—V in FIG. 4.

FIG. 4 shows a perspective view schematically illustrating a configuration of the ECT probe according to another embodiment of the present invention, and FIG. 5 shows a cross-sectional view taken along with line V—V in FIG. 4.

In these figures, reference numeral 41 indicates a flexible substrate formed of an insulative material such as polyimide, 42 indicate a meander-type exciting coil including coil conductors formed as the planar pattern turned back on the opposite surface 41b to the measurement surface 41a of the substrate 41, 43 and 44 indicate a pair of electrode terminals formed on the substrate 41, which is connected electrically to both ends of the exciting coil 42, and 45 and 46 indicate thin-film chips bonded on the exciting coil 42, each of which is mounted with a GMR element (eddy-current sensor) such as an SVMR element, respectively.

The exciting coil 42 includes a coil conductor layer formed on the insulative substrate 41 and an insulating layer covering the coil conductor layer. An exciting part of the exciting coil 42 has a plurality of current lines that extend in parallel with each other to Z direction on the substrate 41, and are turned back at both ends. During testing, alternate exciting currents with opposite directions to each other flow through the current lines adjacent to each other, respectively.

The thin-film chips 45 and 46 are aligned on a central axis of two pairs of current lines 42a and 42b, and 42c and 42d positioned at different locations from each other in the X direction on the exciting coil 42. These thin-film chips 45 and 46 are bonded on the opposite surface to the subject in the exciting coil 42.

Each of the thin-film chips 45 and 46 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, as understood from FIG. 5, the substrate 41 has a non-planar form curved along a traverse direction (X direction) where the measurement surface 41a shows a waveform of two convex-surfaces. The thin-film chips 45 and 46 are mounted, via the exciting coil 42, on the opposite surface 41b of the substrate 41, which has two concave-surface portions corresponding to the two convex-surface portions.

Because the measurement surface 41a on the substrate showing a waveform of the two convex-surfaces has a small facing/contact area with the subject, the sticktion hardly occurs. Even if the sticktion occurs, much less external-force application should be needed to remove the probe from the subject against the sticktion. Consequently, a damage probability by the sticktion is drastically reduced, and therefore, the durability and lifetime can be improved in a large extent. Further, because the thin-film chips 45 and 46 are mounted respectively on the two concave-surfaces of the opposite surface 41b of the substrate 41, the distance between the surface of the subject and the GMR element does not increase, and therefore, a high performance of resolution is provided.

Figure 6:
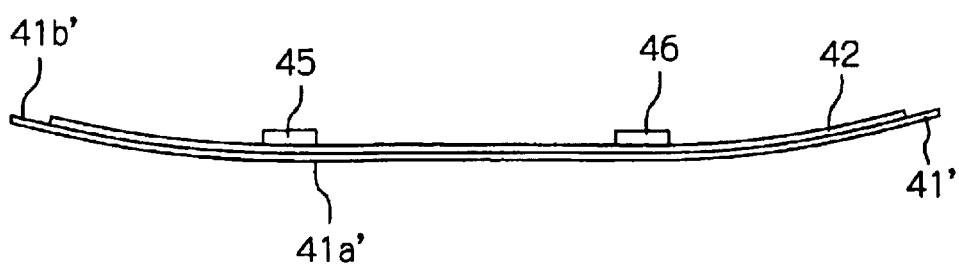
FIG. 6 shows a cross-sectional view schematically illustrating a configuration according to an alternative of the embodiment in FIG. 4.

FIG. 6 shows a cross-sectional view schematically illustrating a configuration according to an alternative of the embodiment in FIG. 4.

According to the alternative, the substrate 41' has a non-planar form curved along a traverse direction (X direction) where the measurement surface 41a' facing to the subject shows a waveform of a single convex-surface that has a planar central portion. The thin-film chips 45 and 46 are mounted, via the exciting coil 42, at the different position from each other on the opposite surface 41b' of the substrate 41', which is a single concave-surface that has a planar central portion corresponding to a single convex-surface that has a planar central portion. The other configurations according to the alternative are almost the same as those according to the embodiment in FIG. 4.

In the alternative, because the measurement surface 41a' on the substrate showing a waveform of a single convex-surface that has a planar central portion has a small facing/contact area with the subject, the sticktion hardly occurs. Even if the sticktion occurs, much less external-force application should be needed to remove the probe from the subject against the sticktion. Consequently, a damage probability by the sticktion is drastically reduced, and therefore, the durability and lifetime can be improved in a large extent. Further, because the thin-film chips 45 and 46 are mounted on the single concave-surface that has a planar central portion of the opposite surface 41b' of the substrate 41', the distance between the surface of the subject and the GMR element does not increase, and therefore, a high performance of resolution is provided.

Figure 7:
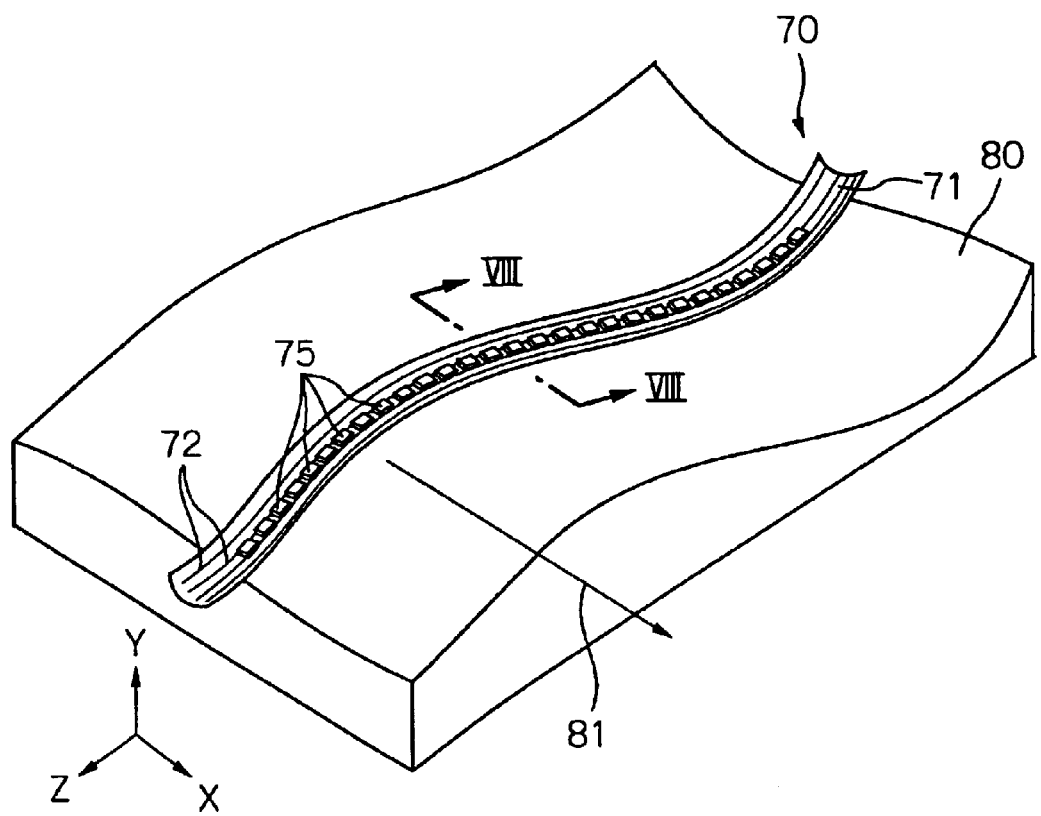
FIG. 7 shows a perspective view schematically illustrating a subject and a configuration of the ECT probe according to a further embodiment of the present invention.
Figure 8:
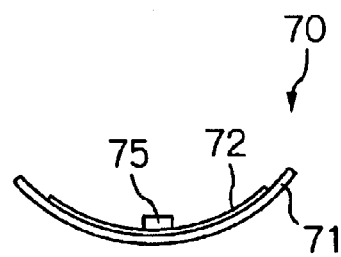
FIG. 8 shows a cross-sectional view taken along with line VIII—VIII in FIG. 7.

FIG. 7 shows a perspective view schematically illustrating a subject and a configuration of the ECT probe according to a further embodiment of the present invention, and FIG. 8 shows a cross-sectional view taken along with line VIII—VIII in FIG. 7.

In these figures, reference numeral 70 indicates a ECT probe, 71 indicates a flexible substrate formed of an insulative material such as polyimide, 72 indicates a meander-type exciting coil including coil conductors formed as the planar pattern turned back on the opposite surface to the measurement surface of the substrate 71, 75 indicates a plurality of thin-film chips bonded on the exciting coil 72, each of which is mounted with a GMR element (eddy-current sensor) such as an SVMR element, and 80 indicates a subject, respectively.

The thin-film chips 75 are aligned on a central axis of a pair of current lines positioned at the center in the X direction on the exciting coil 72. These thin-film chips 75 are bonded on the opposite surface to the subject 80 in the exciting coil 72.

Each of the thin-film chips 75 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, as understood from FIG. 8, the substrate 71 has a non-planar form curved along a traverse direction (X direction) where the measurement surface facing to the subject 80 shows a waveform of a single convex-surface. Further, the substrate 71 has flexibility where the substrate can curve flexibly along the curved surface of the subject 80. The thin-film chips 75 are mounted, via the exciting coil 72, on the opposite surface of the substrate 71, which is a single concave-surface corresponding to the single convex-surface.

The other configurations according to the present embodiment are almost the same as those according to the embodiment in FIG. 1.

Because the measurement surface of the substrate showing a waveform of the single convex-surface has a small facing/contact area with the subject 80, the sticktion hardly occurs. Even if the sticktion occurs, much less external-force application should be needed to remove the probe from the subject 80 against the sticktion. Consequently, a damage probability by the sticktion is drastically reduced, and therefore, the durability and lifetime can be improved in a large extent. Further, because the thin-film chips 75 are mounted on the single concave-surface of the opposite surface of the substrate 71, the distance between the surface of the subject 80 and the GMR element does not increase, and therefore, a high performance of resolution is provided.

Figure 9:
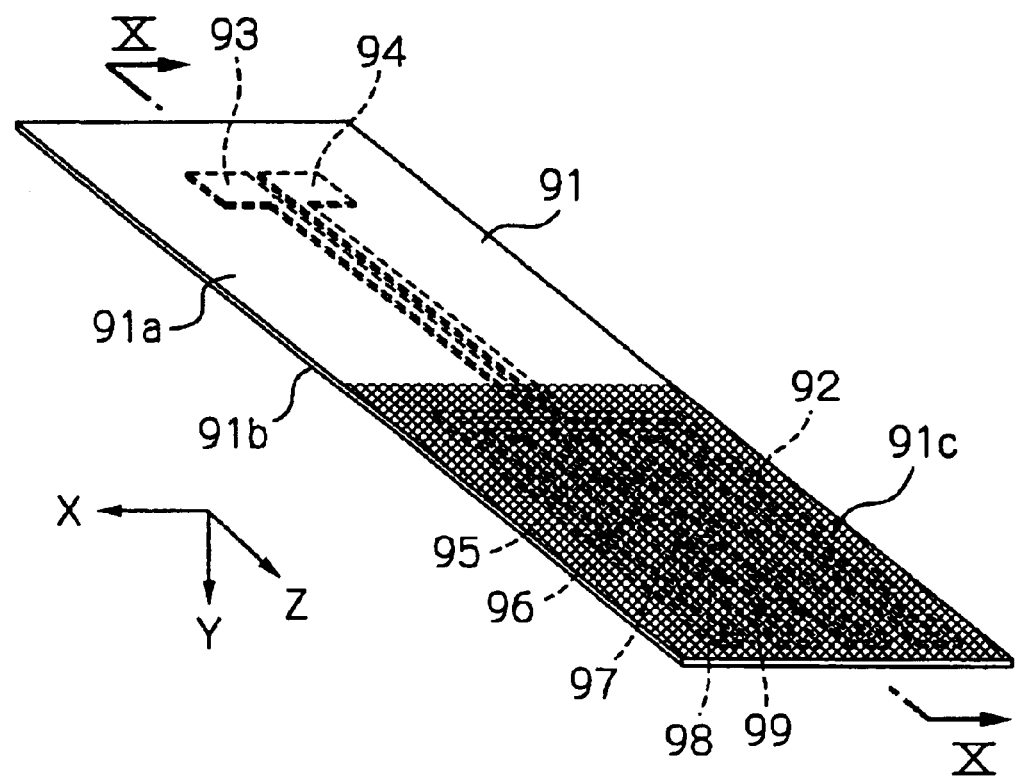
FIG. 9 shows a perspective view schematically illustrating a configuration of the ECT probe according to a still further embodiment of the present invention.
Figure 10:
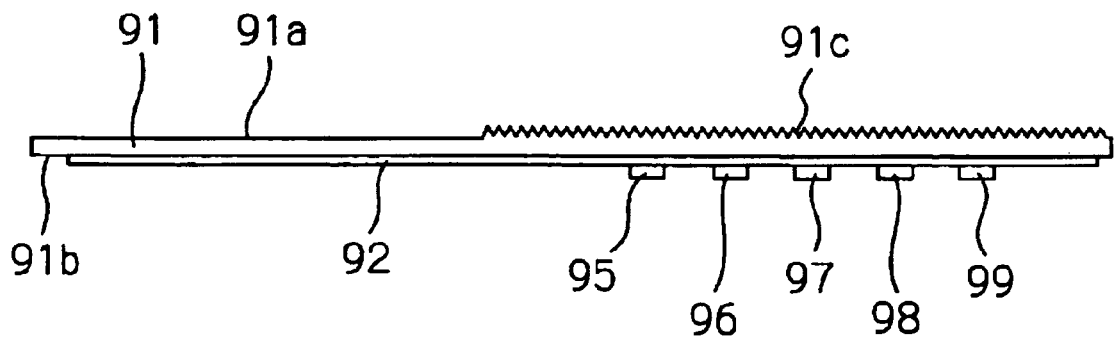
FIG. 10 shows a cross-sectional view taken along with line X—X in FIG. 9.

FIG. 9 shows a perspective view schematically illustrating a configuration of the ECT probe according to a still further embodiment of the present invention, and FIG. 10 shows a cross-sectional view taken along with line X—X in FIG. 9. Here, FIG. 9 shows a view from the side of the opposite surface to that of FIG. 2, that is, of the measurement surface facing to the subject.

In these figures, reference numeral 91 indicates a flexible substrate formed of an insulative material such as polyimide, 92 indicates a meander-type exciting coil including coil conductors formed as the planar pattern turned back on the opposite surface 91b to the measurement surface 91a of the substrate 91, 93 and 94 indicate a pair of electrode terminals formed on the substrate 91, which is connected electrically to both ends of the exciting coil 92, and 95 to 99 indicate thin-film chips bonded on the exciting coil 92, each of which is mounted with a GMR element (eddy-current sensor) such as an SVMR element, respectively.

The exciting coil 92 includes a coil conductor layer formed on the insulative substrate 91 and an insulating layer covering the coil conductor layer. An exciting part of the exciting coil 92 has a plurality of current lines that extend in parallel with each other to Z direction on the substrate 91, and are turned back at both ends. During testing, alternate exciting currents with opposite directions to each other flow through the current lines adjacent to each other, respectively.

The thin-film chips 95 to 99 are aligned on a central axis of a pair of current lines positioned at the center in the X direction on the exciting coil 92. These thin-film chips 95 to 99 are bonded on the opposite surface to the subject in the exciting coil 92.

Each of the thin-film chips 95 to 99 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 91 has a planar form, and a part of the measurement surface 91a facing to subject has a large number of, preferably much small, machined concaves and convexes 91c such as a blasting rough surface or an embossed surface.

Because the measurement surface 91a of the substrate has a large number of machined concaves and convexes 91c, the sticktion hardly occurs. Accordingly, a damage probability by the sticktion is drastically reduced, and therefore, the durability and lifetime can be improved in a large extent.

Figure 11:
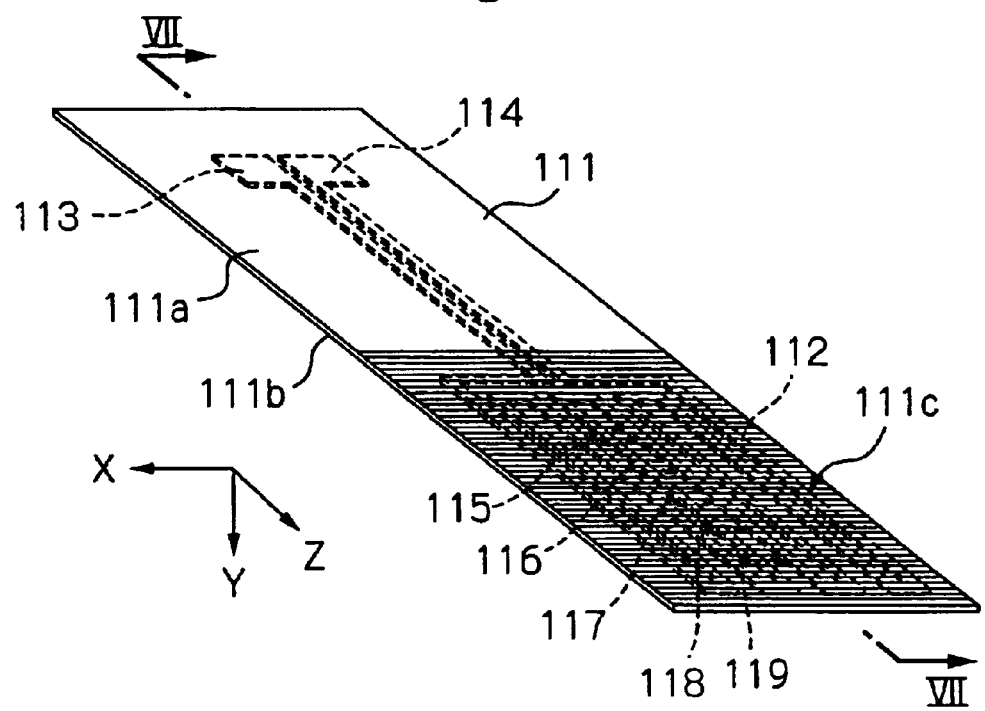
FIG. 11 shows a perspective view schematically illustrating a configuration of the ECT probe according to a still further embodiment of the present invention.
Figure 12:
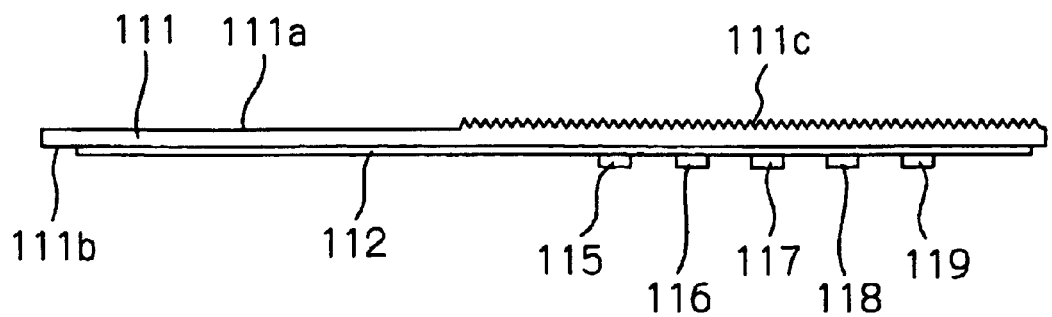
FIG. 12 shows a cross-sectional view taken along with line XII—XII in FIG. 11.

FIG. 11 shows a perspective view schematically illustrating a configuration of the ECT probe according to a still further embodiment of the present invention, and FIG. 12 shows a cross-sectional view taken along with line XII—XII in FIG. 11. Here, FIG. 11 shows a view from the side of the opposite surface to that of FIG. 2, that is, of the measurement surface facing to the subject.

In these figures, reference numeral 111 indicates a flexible substrate formed of an insulative material such as polyimide, 112 indicates a meander-type exciting coil including coil conductors formed as the planar pattern turned back on the opposite surface 111b to the measurement surface 111a of the substrate 111, 113 and 114 indicate a pair of electrode terminals formed on the substrate 111, which is connected electrically to both ends of the exciting coil 112, and 115 to 119 indicate thin-film chips bonded on the exciting coil 112, each of which is mounted with a GMR element (eddy-current sensor) such as an SVMR element, respectively.

The exciting coil 112 includes a coil conductor layer formed on the insulative substrate 111 and an insulating layer covering the coil conductor layer. An exciting part of the exciting coil 112 has a plurality of current lines that extend in parallel with each other to Z direction on the substrate 111, and are turned back at both ends. During testing, alternate exciting currents with opposite directions to each other flow through the current lines adjacent to each other, respectively.

The thin-film chips 115 to 119 are aligned on a central axis of a pair of current lines positioned at the center in the X direction on the exciting coil 112. These thin-film chips 115 to 119 are bonded on the opposite surface to the subject in the exciting coil 112.

Each of the thin-film chips 115 to 119 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 111 has a planar form, and a part of the measurement surface 111*a* facing to subject has a large number of, preferably much small, grooves 111*c* extended along a traverse direction (X direction) in the substrate 111.

Because the measurement surface 111*a* on the substrate has a large number of machined grooves 111*c* extended along the traverse direction, the sticktion hardly occurs. Accordingly, a damage probability by the sticktion is drastically reduced, and therefore, the durability and lifetime can be improved in a large extent.

Figure 13:
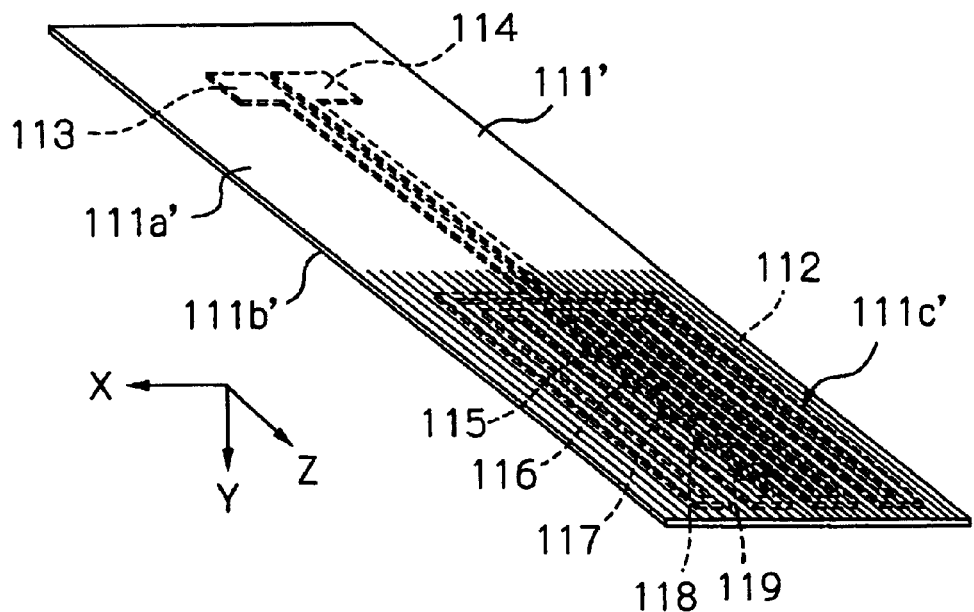
FIG. 13 shows a perspective view schematically illustrating a configuration of the ECT probe according to an alternative of the embodiment in FIG. 11.

FIG. 13 shows a perspective view schematically illustrating a configuration of the ECT probe according to an alternative of the embodiment in FIG. 11. Here, FIG. 13 shows a view from the side of the opposite surface to that of FIG. 2, that is, of the measurement surface facing to the subject.

According to the present alternative, the entire substrate 111' has a planar form, and a part of the measurement surface 111*a*' facing to subject has a large number of, preferably much small, grooves 111*c*' extended along a longitudinal direction (Z direction) in the substrate 111'. The other configurations according to the present alternative are almost the same as those according to the embodiment in FIG. 11.

Because the measurement surface 111*a*' on the substrate has a large number of machined grooves 111*c*' extended along the longitudinal direction, the sticktion hardly occurs. Accordingly, a damage probability by the sticktion is drastically reduced, and therefore, the durability and lifetime can be improved in a large extent.

Figure 14:
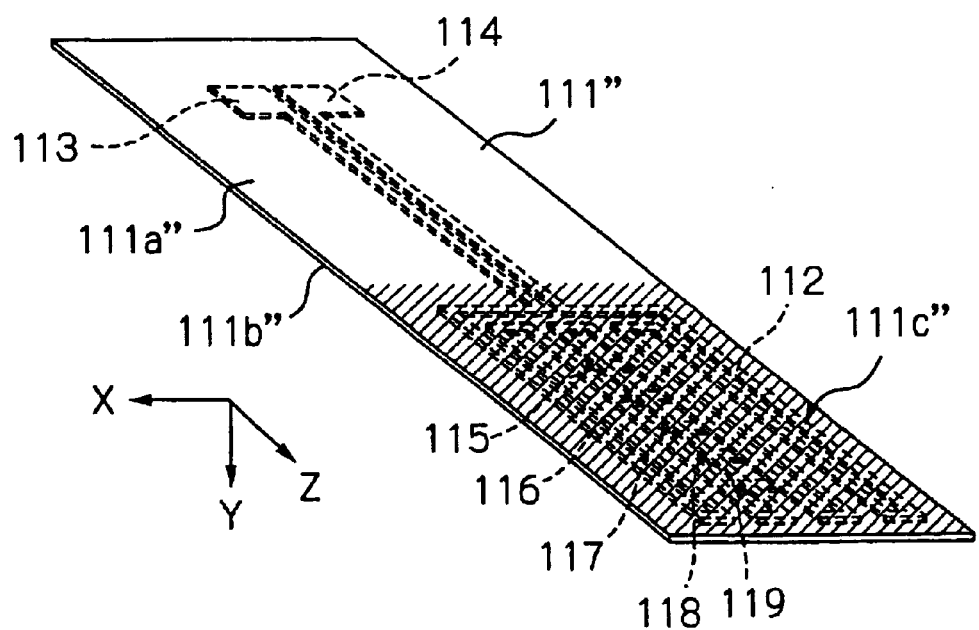
FIG. 14 shows a perspective view schematically illustrating a configuration of the ECT probe according to another alternative of the embodiment in FIG. 11.

FIG. 14 shows a perspective view schematically illustrating a configuration of the ECT probe according to another alternative of the embodiment in FIG. 11. Here, FIG. 14 shows a view from the side of the opposite surface to that of FIG. 2, that is, of the measurement surface facing to the subject.

According to the present alternative, the entire substrate 111" has a planar form, and a part of the measurement surface 111*a*" facing to subject has a large number of, preferably much small, grooves 111*c*" extended along the oblique direction to a traverse direction (X direction) in the substrate 111". The other configurations according to the present alternative are almost the same as those according to the embodiment in FIG. 11.

Because the measurement surface 111*a*" on the substrate has a large number of machined grooves 111*c*" extended along the oblique direction, the sticktion hardly occurs. Accordingly, a damage probability by the sticktion is drastically reduced, and therefore, the durability and lifetime can be improved in a large extent.

Figure 15:
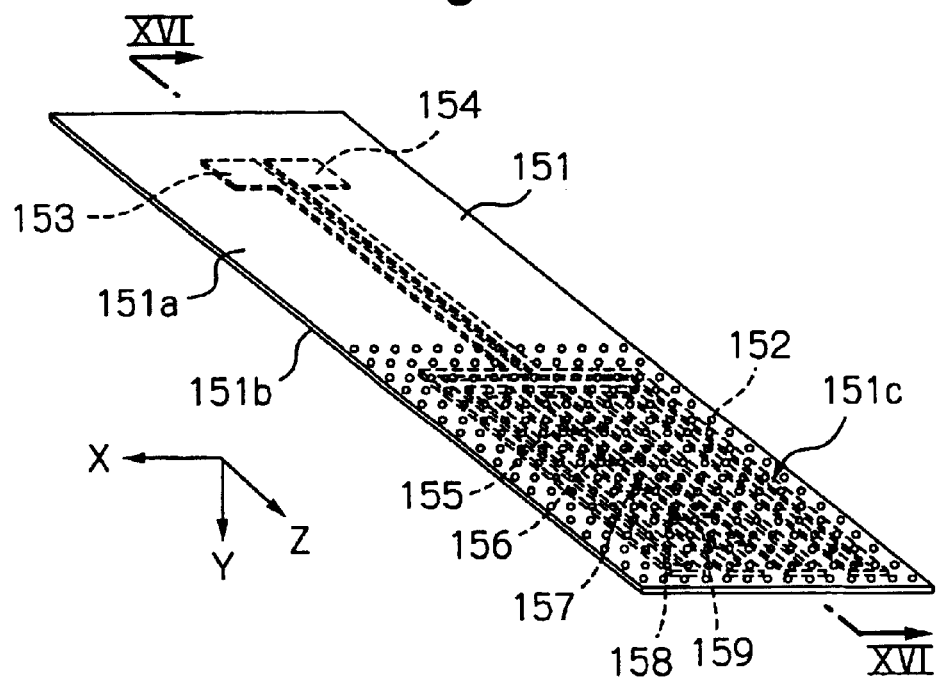
FIG. 15 shows a perspective view schematically illustrating a configuration of the ECT probe according to a still further embodiment of the present invention.
Figure 16:
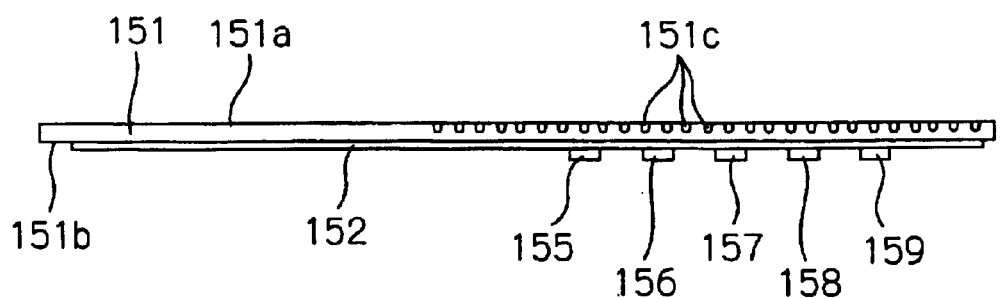
FIG. 16 shows a cross-sectional view taken along with line XVI—XVI in FIG. 15.

FIG. 15 shows a perspective view schematically illustrating a configuration of the ECT probe according to a still further embodiment of the present invention, and FIG. 16 shows a cross-sectional view taken along with line XVI—XVI in FIG. 15. Here, FIG. 15 shows a view from the side of the opposite surface to that of FIG. 2, that is, of the measurement surface facing to the subject.

In these figures, reference numeral 151 indicates a flexible substrate formed of an insulative material such as polyimide, 152 indicates a meander-type exciting coil including coil conductors formed as the planar pattern turned back on the opposite surface 151*b* to the measurement surface 151*a* of the substrate 151, 153 and 154 indicate a pair of electrode terminals formed on the substrate 151, which is connected electrically to both ends of the exciting coil 152, and 155 to 159 indicate thin-film chips bonded on the exciting coil 152, each of which is mounted with a GMR element (eddy-current sensor) such as an SVMR element, respectively.

The exciting coil 152 includes a coil conductor layer formed on the insulative substrate 151 and an insulating layer covering the coil conductor layer. An exciting part of the exciting coil 152 has a plurality of current lines that extend in parallel with each other to Z direction on the substrate 151, and are turned back at both ends. During testing, alternate exciting currents with opposite directions to each other flow through the current lines adjacent to each other, respectively.

The thin-film chips 155 to 159 are aligned on a central axis of a pair of current lines positioned at the center in the X direction on the exciting coil 152. These thin-film chips 155 to 159 are bonded on the opposite surface to the subject in the exciting coil 152.

Each of the thin-film chips 155 to 159 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 151 has a planar form, and a part of the measurement surface 151*a* facing to the subject has a large number of, preferably much small, blind holes 151*c*.

Because the measurement surface 151*a* on the substrate has a large number of machined blind holes 151*c*, the sticktion hardly occurs. Accordingly, a damage probability by the sticktion is drastically reduced, and therefore, the durability and lifetime can be improved in a large extent.

Figure 17:
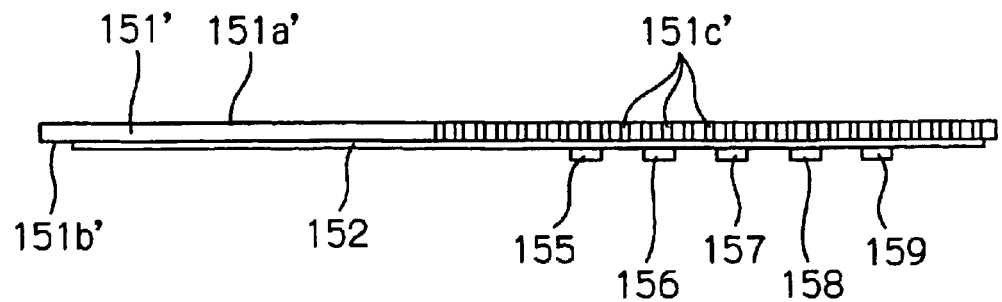
FIG. 17 shows a cross-sectional view schematically illustrating a configuration of the ECT probe according to an alternative of the embodiment in FIG. 15.

FIG. 17 shows a cross-sectional view schematically illustrating a configuration of the ECT probe according to an alternative of the embodiment in FIG. 15.

According to the present alternative, the entire substrate 151' has a planar form, and a part of the measurement surface 151*a*' facing to the subject has a large number of, preferably much small, through holes 151*c*'. The other configurations according to the present alternative are almost the same as those according to the embodiment in FIG. 15.

Because the measurement surface 151*a*' on the substrate has a large number of through holes 151*c*', the sticktion hardly occurs. Accordingly, a damage probability by the sticktion is drastically reduced, and therefore, the durability and lifetime can be improved in a large extent.

Figure 18:
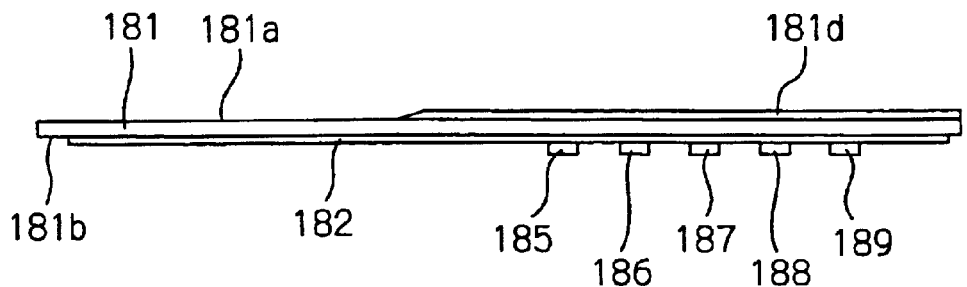
FIG. 18 shows a cross-sectional view schematically illustrating a configuration of the ECT probe according to a still further embodiment of the present invention.

FIG. 18 shows a cross-sectional view schematically illustrating a configuration of the ECT probe according to a still further embodiment of the present invention.

In this figure, reference numeral 181 indicates a flexible substrate formed of an insulative material such as polyimide, 182 indicates a meander-type exciting coil including coil conductors formed as the planar pattern turned back on the opposite surface 181*b* to the measurement surface 181*a* of the substrate 181, and 185 to 189 indicate thin-film chips bonded on the exciting coil 182, each of which is mounted with a GMR element (eddy-current sensor) such as an SVMR element, respectively.

The exciting coil 182 includes a coil conductor layer formed on the insulative substrate 181 and an insulating layer covering the coil conductor layer. An exciting part of the exciting coil 182 has a plurality of current lines that extend in parallel with each other to Z direction on the substrate 181, and are turned back at both ends. During testing, alternate exciting currents with opposite directions to each other flow through the current lines adjacent to each other, respectively.

The thin-film chips 185 to 189 are aligned on a central axis of a pair of current lines positioned at the center in the X direction on the exciting coil 182. These thin-film chips 185 to 189 are bonded on the opposite surface to the subject in the exciting coil 182.

Each of the thin-film chips 185 to 189 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 181 has a planar form, and a part of the measurement surface 181a facing to the subject is applied with a lubricant 181d such as a lubricating oil. The other configurations according to the present alternative are almost the same as those according to the embodiment in FIG. 1 with the exception that the substrate 181 has a planar form.

Because a part of the measurement surface 181a on the substrate has a lubricant layer 181d, the sticktion hardly occurs. Accordingly, a damage probability by the sticktion is drastically reduced, and therefore, the durability and lifetime can be improved in a large extent.

Figure 19:
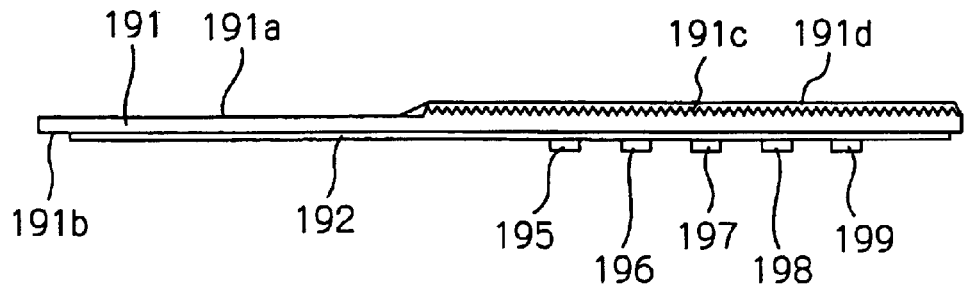
FIG. 19 shows a cross-sectional view schematically illustrating a configuration of the ECT probe according to a further embodiment of the present invention.

FIG. 19 shows a cross-sectional view schematically illustrating a configuration of the ECT probe according to a still further embodiment of the present invention.

In this figure, reference numeral 191 indicates a flexible substrate formed of an insulative material such as polyimide, 192 indicates a meander-type exciting coil including coil conductors formed as the planar pattern turned back on the opposite surface 191b to the measurement surface 191a of the substrate 191, and 195 to 199 indicate thin-film chips bonded on the exciting coil 192, each of which is mounted with a GMR element (eddy-current sensor) such as an SVMR element, respectively.

The exciting coil 192 includes a coil conductor layer formed on the insulative substrate 191 and an insulating layer covering the coil conductor layer. An exciting part of the exciting coil 192 has a plurality of current lines that extend in parallel with each other to Z direction on the substrate 191, and are turned back at both ends. During testing, alternate exciting currents with opposite directions to each other flow through the current lines adjacent to each other, respectively.

The thin-film chips 195 to 199 are aligned on a central axis of a pair of current lines positioned at the center in the X direction on the exciting coil 192. These thin-film chips 195 to 199 are bonded on the opposite surface to the subject in the exciting coil 192.

Each of the thin-film chips 195 to 199 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 191 has a planar form, and a part of the measurement surface 191a facing to the subject has a large number of, preferably much small, grooves 191c extended along a traverse direction (X direction), a longitudinal direction (Z direction) or an oblique direction to the traverse direction (X direction), and is applied with a lubricant 191d such as a lubricating oil. The other configurations according to the present embodiment are almost the same as those according to the embodiment in FIG. 11, or the alternative in FIG. 13 or in FIG. 14.

Because a part of the measurement surface 191a on the substrate has a large number of grooves 191c and a lubricant layer 191d, the sticktion hardly occurs. Accordingly, a damage probability by the sticktion is drastically reduced, and therefore, the durability and lifetime can be improved in a large extent.

Figure 20:
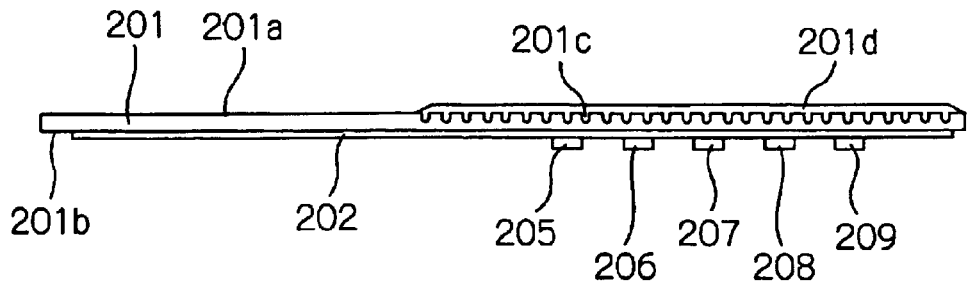
FIG. 20 shows a cross-sectional view schematically illustrating a configuration of the ECT probe according to a still further embodiment of the present invention.

FIG. 20 shows a cross-sectional view schematically illustrating a configuration of the ECT probe according to a still further embodiment of the present invention.

In this figure, reference numeral 201 indicates a flexible substrate formed of an insulative material such as polyimide, 202 indicates a meander-type exciting coil including coil conductors formed as the planar pattern turned back on the opposite surface 201b to the measurement surface 201a of the substrate 201, and 205 to 209 indicate thin-film chips bonded on the exciting coil 202, each of which is mounted with a GMR element (eddy-current sensor) such as an SVMR element, respectively.

The exciting coil 202 includes a coil conductor layer formed on the insulative substrate 201 and an insulating layer covering the coil conductor layer. An exciting part of the exciting coil 202 has a plurality of current lines that extend in parallel with each other to Z direction on the substrate 201, and are turned back at both ends. During testing, alternate exciting currents with opposite directions to each other flow through the current lines adjacent to each other, respectively.

The thin-film chips 205 to 209 are aligned on a central axis of a pair of current lines positioned at the center in the X direction on the exciting coil 202. These thin-film chips 205 to 209 are bonded on the opposite surface to the subject in the exciting coil 202.

Each of the thin-film chips 205 to 209 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 201 has a planar form, and a part of the measurement surface 201a facing to the subject has a large number of, preferably much small, blind holes 201c, and is applied with a lubricant 201d such as a lubricating oil. The other configurations according to the present embodiment are almost the same as those according to the embodiment in FIG. 15.

Because a part of the measurement surface 201a on the substrate has a large number of blind holes 201c and a lubricant layer 201d, the sticktion hardly occurs. Accordingly, a damage probability by the sticktion is drastically reduced, and therefore, the durability and lifetime can be improved in a large extent.

Figure 21:
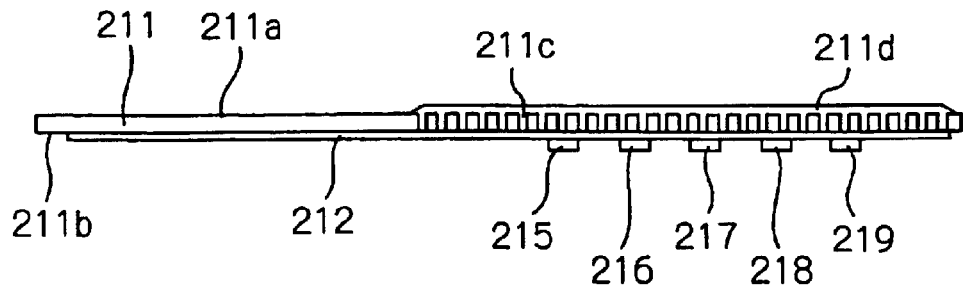
FIG. 21 shows a cross-sectional view schematically illustrating a configuration of the ECT probe according to a still further embodiment of the present invention.

FIG. 21 shows a cross-sectional view schematically illustrating a configuration of the ECT probe according to a still further embodiment of the present invention.

In this figure, reference numeral 211 indicates a flexible substrate formed of an insulative material such as polyimide, 212 indicates a meander-type exciting coil including coil conductors formed as the planar pattern turned back on the opposite surface 211b to the measurement surface 211a of the substrate 211, and 215 to 219 indicate thin-film chips bonded on the exciting coil 212, each of which is mounted with a GMR element (eddy-current sensor) such as an SVMR element, respectively.

The exciting coil 212 includes a coil conductor layer formed on the insulative substrate 211 and an insulating layer covering the coil conductor layer. An exciting part of the exciting coil 212 has a plurality of current lines that extend in parallel with each other to Z direction on the substrate 211, and are turned back at both ends. During testing, alternate exciting currents with opposite directions to each other flow through the current lines adjacent to each other, respectively.

The thin-film chips 215 to 219 are aligned on a central axis of a pair of current lines positioned at the center in the X direction on the exciting coil 212. These thin-film chips 215 to 219 are bonded on the opposite surface to the subject in the exciting coil 212.

Each of the thin-film chips 215 to 219 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 211 has a planar form, and a part of the measurement surface 211*a* facing to the subject has a large number of, preferably much small, through holes, and is applied with a lubricant 211*d* such as a lubricating oil. The other configurations according to the present embodiment are almost the same as those according to the embodiment in FIG. 17.

Because a part of the measurement surface 211*a* on the substrate has a large number of through holes 211*c* and a lubricant layer 211*d*, the sticktion hardly occurs. Accordingly, a damage probability by the sticktion is drastically reduced, and therefore, the durability and lifetime can be improved in a large extent.

Figure 22:
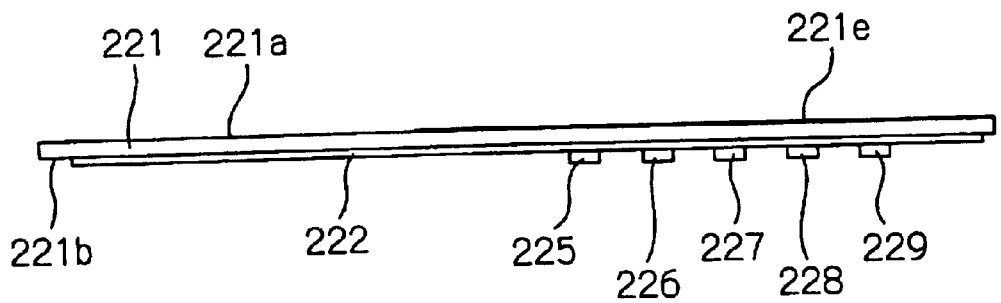
FIG. 22 shows a cross-sectional view schematically illustrating a configuration of the ECT probe according to a still further embodiment of the present invention.

FIG. 22 shows a cross-sectional view schematically illustrating a configuration of the ECT probe according to a still further embodiment of the present invention.

In this figure, reference numeral 221 indicates a flexible substrate formed of an insulative material such as polyimide, 222 indicates a meander-type exciting coil including coil conductors formed as the planar pattern turned back on the opposite surface 221*b* to the measurement surface 221*a* of the substrate 221, and 225 to 229 indicate thin-film chips bonded on the exciting coil 222, each of which is mounted with a GMR element (eddy-current sensor) such as an SVMR element, respectively.

The exciting coil 222 includes a coil conductor layer formed on the insulative substrate 221 and an insulating layer covering the coil conductor layer. An exciting part of the exciting coil 222 has a plurality of current lines that extend in parallel with each other to Z direction on the substrate 221, and are turned back at both ends. During testing, alternate exciting currents with opposite directions to each other flow through the current lines adjacent to each other, respectively.

The thin-film chips 225 to 229 are aligned on a central axis of a pair of current lines positioned at the center in the X direction on the exciting coil 222. These thin-film chips 225 to 229 are bonded on the opposite surface to the subject in the exciting coil 222.

Each of the thin-film chips 225 to 229 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 221 has a planar form, and a part of the measurement surface 211*a* facing to the subject is coated with a DLC layer 221*e*. The other configurations according to the present embodiment are almost the same as those according to the embodiment in FIG. 1 or the embodiment in FIG. 18 with the exception that the substrate 221 has a planar form.

Because a part of the measurement surface 221*a* on the substrate has a DLC layer 221*e*, the sticktion hardly occurs. Accordingly, a damage probability by the sticktion is drastically reduced, and therefore, the durability and lifetime can be improved in a large extent.

Figure 23:
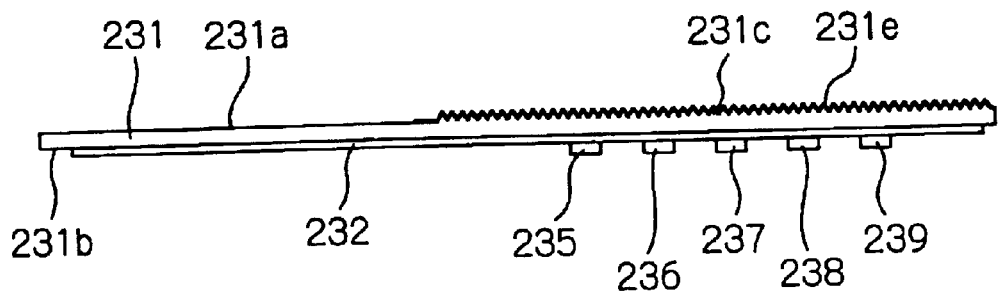
FIG. 23 shows a cross-sectional view schematically illustrating a configuration of the ECT probe according to a still further embodiment of the present invention.

FIG. 23 shows a cross-sectional view schematically illustrating a configuration of the ECT probe according to a still further embodiment of the present invention.

In this figure, reference numeral 231 indicates a flexible substrate formed of an insulative material such as polyimide, 232 indicates a meander-type exciting coil including coil conductors formed as the planar pattern turned back on the opposite surface 231*b* to the measurement surface 231*a* of the substrate 231, and 235 to 239 indicate thin-film chips bonded on the exciting coil 232, each of which is mounted with a GMR element (eddy-current sensor) such as an SVMR element, respectively.

The exciting coil 232 includes a coil conductor layer formed on the insulative substrate 231 and an insulating layer covering the coil conductor layer. An exciting part of the exciting coil 232 has a plurality of current lines that extend in parallel with each other to Z direction on the substrate 231, and are turned back at both ends. During testing, alternate exciting currents with opposite directions to each other flow through the current lines adjacent to each other, respectively.

The thin-film chips 235 to 239 are aligned on a central axis of a pair of current lines positioned at the center in the X direction on the exciting coil 232. These thin-film chips 235 to 239 are bonded on the opposite surface to the subject in the exciting coil 232.

Each of the thin-film chips 235 to 239 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 231 has a planar form, and a part of the measurement surface 231*a* facing to the subject has a large number of, preferably much small, grooves 231*c* extended along a traverse direction (X direction), a longitudinal direction (Z direction) or an oblique direction to the traverse direction (X direction), and is coated with a DLC layer 231*e*. The other configurations according to the present embodiment are almost the same as those according to the embodiment in FIG. 11, or the alternative in FIG. 13 or in FIG. 14.

Because a part of the measurement surface 231*a* on the substrate has a large number of grooves 231*c* and a DLC layer 231*e*, the sticktion hardly occurs. Accordingly, a damage probability by the sticktion is drastically reduced, and therefore, the durability and lifetime can be improved in a large extent.

Figure 24:
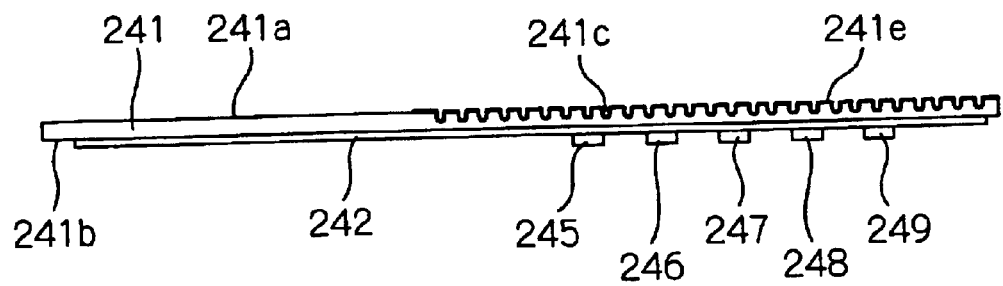
FIG. 24 shows a cross-sectional view schematically illustrating a configuration of the ECT probe according to a still further embodiment of the present invention.

FIG. 24 shows a cross-sectional view schematically illustrating a configuration of the ECT probe according to a still further embodiment of the present invention.

In this figure, reference numeral 241 indicates a flexible substrate formed of an insulative material such as polyimide, 242 indicates a meander-type exciting coil including coil conductors formed as the planar pattern turned back on the opposite surface 241*b* to the measurement surface 241*a* of the substrate 241, and 245 to 249 indicate thin-film chips bonded on the exciting coil 242, each of which is mounted with a GMR element (eddy-current sensor) such as an SVMR element, respectively.

The exciting coil 242 includes a coil conductor layer formed on the insulative substrate 241 and an insulating layer covering the coil conductor layer. An exciting part of the exciting coil 242 has a plurality of current lines that extend in parallel with each other to Z direction on the substrate 241, and are turned back at both ends. During testing, alternate exciting currents with opposite directions to each other flow through the current lines adjacent to each other, respectively.

The thin-film chips 245 to 249 are aligned on a central axis of a pair of current lines positioned at the center in the X direction on the exciting coil 242. These thin-film chips 245 to 249 are bonded on the opposite surface to the subject in the exciting coil 242.

Each of the thin-film chips 245 to 249 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 241 has a planar form, and a part of the measurement surface 241a facing to the subject has a large number of, preferably much small, blind holes 241c, and is coated with a DLC layer 241e. The other configurations according to the present embodiment are almost the same as those according to the embodiment in FIG. 15.

Because a part of the measurement surface 241a on the substrate has a large number of blind holes 241c and a DLC layer 241e, the sticktion hardly occurs. Accordingly, a damage probability by the sticktion is drastically reduced, and therefore, the durability and lifetime can be improved in a large extent.

Figure 25:
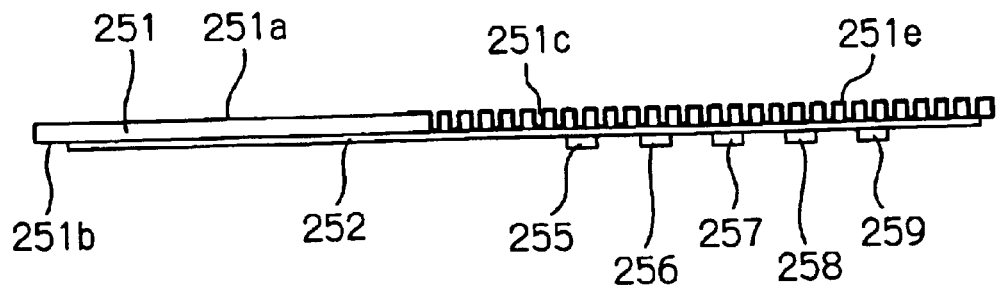
FIG. 25 shows a cross-sectional view schematically illustrating a configuration of the ECT probe according to a still further embodiment of the present invention.

FIG. 25 shows a cross-sectional view schematically illustrating a configuration of the ECT probe according to a still further embodiment of the present invention.

In this figure, reference numeral 251 indicates a flexible substrate formed of an insulative material such as polyimide, 252 indicates a meander-type exciting coil including coil conductors formed as the planar pattern turned back on the opposite surface 251b to the measurement surface 251a of the substrate 251, and 255 to 259 indicate thin-film chips bonded on the exciting coil 252, each of which is mounted with a GMR element (eddy-current sensor) such as an SVMR element, respectively.

The exciting coil 252 includes a coil conductor layer formed on the insulative substrate 251 and an insulating layer covering the coil conductor layer. An exciting part of the exciting coil 252 has a plurality of current lines that extend in parallel with each other to Z direction on the substrate 251, and are turned back at both ends. During testing, alternate exciting currents with opposite directions to each other flow through the current lines adjacent to each other, respectively.

The thin-film chips 255 to 259 are aligned on a central axis of a pair of current lines positioned at the center in the X direction on the exciting coil 252. These thin-film chips 255 to 259 are bonded on the opposite surface to the subject in the exciting coil 252.

Each of the thin-film chips 255 to 259 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 251 has a planar form, and a part of the measurement surface 251a facing to the subject has a large number of, preferably much small, through holes 251c, and is applied with a DLC layer 251e. The other configurations according to the present embodiment are almost the same as those according to the alternative in FIG. 17.

Because a part of the measurement surface 251a on the substrate has a large number of through holes 251c and a DLC layer 251e, the sticktion hardly occurs. Accordingly, a damage probability by the sticktion is drastically reduced, and therefore, the durability and lifetime can be improved in a large extent.

Figure 26:
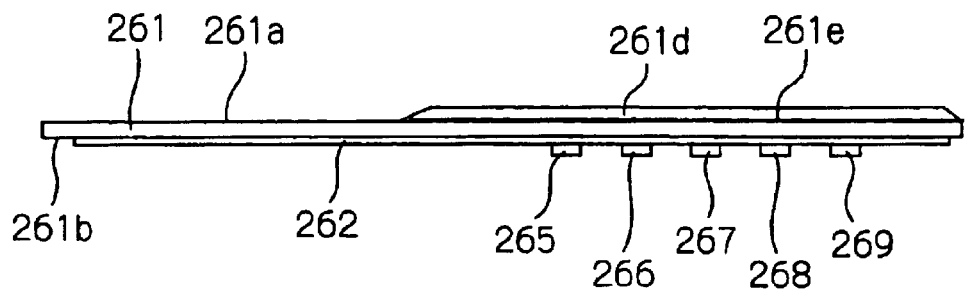
FIG. 26 shows a cross-sectional view schematically illustrating a configuration of the ECT probe according to a still further embodiment of the present invention.

FIG. 26 shows a cross-sectional view schematically illustrating a configuration of the ECT probe according to a still further embodiment of the present invention.

In this figure, reference numeral 261 indicates a flexible substrate formed of an insulative material such as polyimide, 262 indicates a meander-type exciting coil including coil conductors formed as the planar pattern turned back on the opposite surface 261b to the measurement surface 261a of the substrate 261, and 265 to 269 indicate thin-film chips bonded on the exciting coil 262, each of which is mounted with a GMR element (eddy-current sensor) such as an SVMR element, respectively.

The exciting coil 262 includes a coil conductor layer formed on the insulative substrate 261 and an insulating layer covering the coil conductor layer. An exciting part of the exciting coil 262 has a plurality of current lines that extend in parallel with each other to Z direction on the substrate 261, and are turned back at both ends. During testing, alternate exciting currents with opposite directions to each other flow through the current lines adjacent to each other, respectively.

The thin-film chips 265 to 269 are aligned on a central axis of a pair of current lines positioned at the center in the X direction on the exciting coil 262. These thin-film chips 265 to 269 are bonded on the opposite surface to the subject in the exciting coil 262.

Each of the thin-film chips 265 to 269 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 261 has a planar form, and a part of the measurement surface 261a facing to the subject is coated with a DLC layer 261e, and is applied with a lubricant 261d such as a lubricating oil. The other configurations according to the present embodiment are almost the same as those according to the embodiment in FIG. 1 or the embodiment in FIG. 18 with the exception that the substrate 261 has a planar form.

Because a part of the measurement surface 261a on the substrate has a DLC layer 261e and a lubricant layer 261d, the sticktion hardly occurs. Accordingly, a damage probability by the sticktion is drastically reduced, and therefore, the durability and lifetime can be improved in a large extent.

Figure 27:
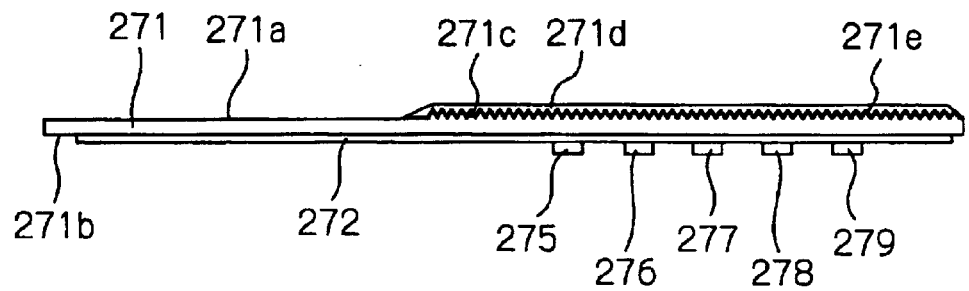
FIG. 27 shows a cross-sectional view schematically illustrating a configuration of the ECT probe according to a still further embodiment of the present invention.

FIG. 27 shows a cross-sectional view schematically illustrating a configuration of the ECT probe according to a still further embodiment of the present invention.

In this figure, reference numeral 271 indicates a flexible substrate formed of an insulative material such as polyimide, 272 indicates a meander-type exciting coil including coil conductors formed as the planar pattern turned back on the opposite surface 271b to the measurement surface 271a of the substrate 271, and 275 to 279 indicate thin-film chips bonded on the exciting coil 272, each of which is mounted with a GMR element (eddy-current sensor) such as an SVMR element, respectively.

The exciting coil 272 includes a coil conductor layer formed on the insulative substrate 271 and an insulating layer covering the coil conductor layer. An exciting part of the exciting coil 272 has a plurality of current lines that extend in parallel with each other to Z direction on the substrate 271, and are turned back at both ends. During testing, alternate exciting currents with opposite directions to each other flow through the current lines adjacent to each other, respectively.

The thin-film chips 275 to 279 are aligned on a central axis of a pair of current lines positioned at the center in the X direction on the exciting coil 272. These thin-film chips 275 to 279 are bonded on the opposite surface to the subject in the exciting coil 272.

Each of the thin-film chips 275 to 279 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 271 has a planar form, and a part of the measurement surface 271a facing to the subject has a large number of, preferably much small, grooves 271c extended along a traverse direction (X direction), a longitudinal direction (Z direction) or an oblique direction to the traverse direction (X direction), and is coated with a DLC layer 271e, and is further applied with a lubricant 271d such as a lubricating oil. The other configurations according to the present embodiment are almost the same as those according to the embodiment in FIG. 11, or the alternative in FIG. 13 or in FIG. 14.

Because a part of the measurement surface 271a on the substrate has a large number of grooves 271c, a DLC layer 271e and a lubricant layer 271d, the sticktion hardly occurs. Accordingly, a damage probability by the sticktion is drastically reduced, and therefore, the durability and lifetime can be improved in a large extent.

Figure 28:
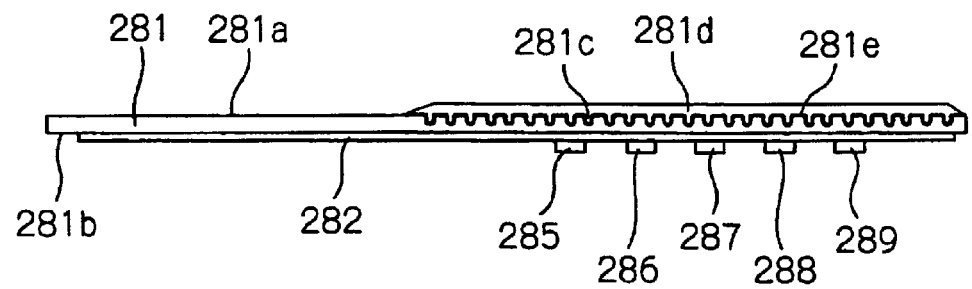
FIG. 28 shows a cross-sectional view schematically illustrating a configuration of the ECT probe according to a still further embodiment of the present invention.

FIG. 28 shows a cross-sectional view schematically illustrating a configuration of the ECT probe according to a still further embodiment of the present invention.

In this figure, reference numeral 281 indicates a flexible substrate formed of an insulative material such as polyimide, 282 indicates a meander-type exciting coil including coil conductors formed as the planar pattern turned back on the opposite surface 281b to the measurement surface 281a of the substrate 281, and 285 to 289 indicate thin-film chips bonded on the exciting coil 282, each of which is mounted with a GMR element (eddy-current sensor) such as an SVMR element, respectively.

The exciting coil 282 includes a coil conductor layer formed on the insulative substrate 281 and an insulating layer covering the coil conductor layer. An exciting part of the exciting coil 282 has a plurality of current lines that extend in parallel with each other to Z direction on the substrate 281, and are turned back at both ends. During testing, alternate exciting currents with opposite directions to each other flow through the current lines adjacent to each other, respectively.

The thin-film chips 285 to 289 are aligned on a central axis of a pair of current lines positioned at the center in the X direction on the exciting coil 282. These thin-film chips 285 to 289 are bonded on the opposite surface to the subject in the exciting coil 282.

Each of the thin-film chips 285 to 289 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 281 has a planar form, and a part of the measurement surface 281a facing to the subject has a large number of, preferably much small, blind holes 281c, and is coated with a DLC layer 281c, and is further applied with a lubricant 281d such as a lubricating oil. The other configurations according to the present embodiment are almost the same as those according to the embodiment in FIG. 15.

Because a part of the measurement surface 281a on the substrate has a large number of blind holes 281c, a DLC layer 281e and a lubricant layer 281d, the sticktion hardly occurs. Accordingly, a damage probability by the sticktion is drastically reduced, and therefore, the durability and lifetime can be improved in a large extent.

Figure 29:
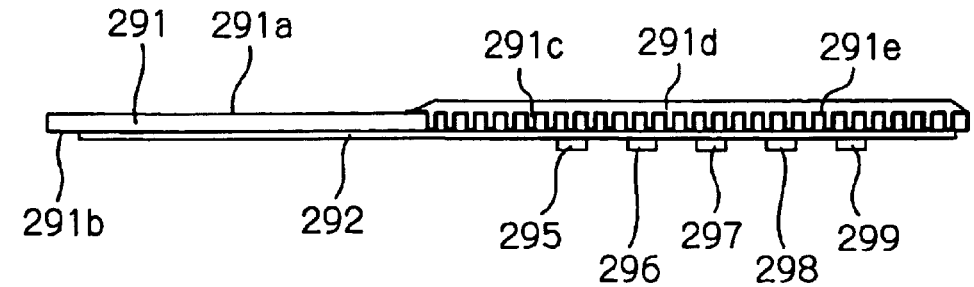
FIG. 29 shows a cross-sectional view schematically illustrating a configuration of the ECT probe according to a still further embodiment of the present invention.

FIG. 29 shows a cross-sectional view schematically illustrating a configuration of the ECT probe according to a still further embodiment of the present invention.

In this figure, reference numeral 291 indicates a flexible substrate formed of an insulative material such as polyimide, 292 indicates a meander-type exciting coil including coil conductors formed as the planar pattern turned back on the opposite surface 291b to the measurement surface 291a of the substrate 291, and 295 to 299 indicate thin-film chips bonded on the exciting coil 292, each of which is mounted with a GMR element (eddy-current sensor) such as an SVMR element, respectively.

The exciting coil 292 includes a coil conductor layer formed on the insulative substrate 291 and an insulating layer covering the coil conductor layer. An exciting part of the exciting coil 292 has a plurality of current lines that extend in parallel with each other to Z direction on the substrate 291, and are turned back at both ends. During testing, alternate exciting currents with opposite directions to each other flow through the current lines adjacent to each other, respectively.

The thin-film chips 295 to 299 are aligned on a central axis of a pair of current lines positioned at the center in the X direction on the exciting coil 292. These thin-film chips 295 to 299 are bonded on the opposite surface to the subject in the exciting coil 292.

Each of the thin-film chips 295 to 299 includes a GMR element such as an SVMR element for example, a pair of lead conductors connected electrically to the GMR element, and a pair of electrode terminals connected electrically to the lead conductors, all of which are formed by thin-film technique on a chip substrate.

According to the present embodiment, the entire substrate 291 has a planar form, and a part of the measurement surface 291a facing to the subject has a large number of, preferably much small, through holes 291c, and is coated with a DLC layer 291c, and is further applied with a lubricant 291d such as a lubricating oil. The other configurations according to the present embodiment are almost the same as those according to the alternative in FIG. 17.

Because a part of the measurement surface 291a on the substrate has a large number of through holes 291c, a DLC layer 291e and a lubricant layer 291d, the sticktion hardly occurs. Accordingly, a damage probability by the sticktion is drastically reduced, and therefore, the durability and lifetime can be improved in a large extent.

In the above-mentioned embodiments, the thin-film chip includes the GMR element such as the SVMR element. However, it is evident that the thin-film chip may include a TMR element instead of the GMR element, which has higher sensitivity than the GMR element.

Further, it is also evident that the detection coil with high sensitivity may be used instead of the GMR element.

All the foregoing embodiments are by way of example of the present invention only and not intended to be limiting, and many widely different alternations and modifications of the present invention may be constructed. Accordingly, the present invention is limited only as defined in the following claims and equivalents thereto.

The eddy-current probe according to the present invention is extremely useful for a remarkably fine nondestructive testing such as an inspection of the micro-defects, the cracks, the scratches and so on in an object's surface and inside and an inspection of the micropatterns on a printed circuit board, as well as nondestructive testing of distorted surfaces of important metal machine parts of a nuclear power plant, an aircraft and so on, such as turbine blades, various pipes and airplane wings.

What is claimed is:

1. An eddy-current probe comprising:
   a substrate having a first surface facing to a subject to be tested and a second surface opposite to said first surface;
   an exciting coil formed on said second surface, having a pair of current lines in parallel with each other through which exciting currents flow in opposite directions to each other during testing, for generating an alternate magnetic field applied to said subject by said exciting currents;
   at least one eddy-current sensor positioned on a central axis between said pair of current lines on said second surface of said substrate, for detecting a magnetic field generated newly from said subject by an eddy-current induced by said alternate magnetic field;
   said substrate having a non-planar form having at least one convex-surface portion on said first surface; and
   said at least one eddy-current sensor formed on at least one concave-surface portion formed on said second surface, which is corresponding to said at least one convex-surface portion.

2. The eddy-current probe as claimed in claim 1, wherein said at least one convex-surface portion has a waved convex form where said substrate is curved along a traverse direction.

3. The eddy-current probe as claimed in claim 1, wherein said at least one convex-surface portion is a single convex-surface portion.

4. The eddy-current probe as claimed in claim 1, wherein said at least one convex-surface portion is a plurality of convex-surface portions.

5. The eddy-current probe as claimed in claim 1, wherein said substrate is a flexible substrate.

6. The eddy-current probe as claimed in claim 1, wherein said at least one eddy-current sensor is a single eddy-current sensor aligned on said central axis between said pair of current lines.

7. The eddy-current probe as claimed in claim 1, wherein said at least one eddy-current sensor is a plurality of eddy-current sensors aligned on said central axis between said pair of current lines.

8. The eddy-current probe as claimed in claim 1, wherein said at least one eddy-current sensor is a magnetoresistive element.

9. The eddy-current probe as claimed in claim 8, wherein said magnetoresistive element is a giant magnetoresistive element or a tunnel magnetoresistive element.

10. The eddy-current probe as claimed in claim 1, wherein said at least one eddy-current sensor is a detection coil.

11. The eddy-current probe as claimed in claim 1, wherein said exciting coil is a meander-type coil.

12. The eddy-current probe as claimed in claim 1, wherein said exciting coil comprises a coil conductor layer formed on said substrate and an insulating layer covering said coil conductor layer.

* * * * *